United States Patent
Lee et al.

(10) Patent No.: US 6,933,403 B2
(45) Date of Patent: Aug. 23, 2005

(54) MONO CARBONYLATION OF BENZENE DIOLS

(75) Inventors: Yeon-Soo Lee, Daejeon (KR); Bum-Tae Kim, Daejeon (KR); Yong-Ki Min, Daejeon (KR); No-Kyun Park, Daejeon (KR); Ki-Ho Kim, Chunan (KR); Ki-Soo Kim, Suwon (KR)

(73) Assignees: Bioland Co., Ltd., Chunan (KR); Korea Research Institute of Chemical Technology, Daejon (KR)

( * ) Notice: Subject to any disclaimer, the term of this patent is extended or adjusted under 35 U.S.C. 154(b) by 0 days.

(21) Appl. No.: 10/490,673

(22) PCT Filed: Oct. 14, 2002

(86) PCT No.: PCT/KR02/01915
§ 371 (c)(1),
(2), (4) Date: Mar. 24, 2004

(87) PCT Pub. No.: WO03/033449
PCT Pub. Date: Apr. 24, 2003

(65) Prior Publication Data
US 2004/0260114 A1 Dec. 23, 2004

(30) Foreign Application Priority Data
Oct. 17, 2001 (KR) .......................... 2001-64008

(51) Int. Cl.[7] ............................................. C07C 67/313
(52) U.S. Cl. ............................................. 560/144
(58) Field of Search .................................. 560/144

(56) References Cited
FOREIGN PATENT DOCUMENTS

| EP | 178929 A1 | 4/1986 |
|---|---|---|
| JP | 62-249945 A | 10/1987 |
| JP | 5-140035 A | 6/1993 |

OTHER PUBLICATIONS

Xia et al., "Study on Synthesis of 1,4–Benzenediol Monoacetate", Journal of China University of Mining & Technology 2001: 30(6), 11–12.
Tangestaninejad et al., "Rapid and Efficient Acetylation of Alcohols and Phenols with Acetic Anhydride Using Tin(IV) Porphyrin as Catalyst", Synthetic Communications, 2002: 32(9), 1337–1343.

Primary Examiner—Kamal A. Saeed
(74) Attorney, Agent, or Firm—Henry D. Coleman; R. Neil Sudol; William J. Sapone

(57) ABSTRACT

A process for a mono carbonylation of a benzenediol of the formula (I) is characterized in that a benzene diol of the formula (II) is reacted with an acid anhydride or carbonyl halide of the formula (III) without any organic or inorganic bases for thereby producing a monocarbonylated benzenediol of the formula (I):

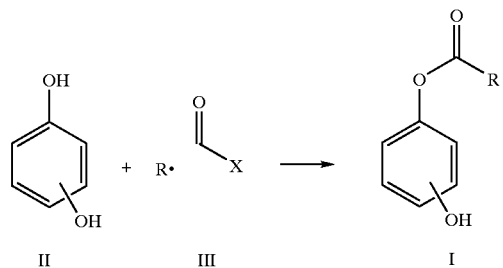

wherein R is hydrogen, $C_1$–$C_{15}$ alkyl group, cycle alkyl group, aryl group, alkoxy group, aryloxy group, dialkylamino group, alkylarylamino group or diarylamino group, and X is a general leaving group such as fluoride, chloride, bromide, iodide, acetoxy, etc.

12 Claims, No Drawings

MONO CARBONYLATION OF BENZENE DIOLS

BACKGROUND OF THE INVENTION

1. Field of the Invention

The present invention relates to a mono carbonylation process of benzene diols, and in particular to a process for mono carbonylation of benzene diols which is characterized in that a mono protected benzene diol is prepared in high yield by reacting hydroquinone with acid anhydride or carbonylhalide without any bases in accordance with a protective reaction of hydroquinone which is widely used in a fine chemical industry.

2. Description of the Background Art

Benzene diol has two equivalent hydroxyl groups, so it is hard to adapt a substitutent selectively. In particular, mono acetyl hydroquinone is a compound (Korean patent application No. 2000-27129, U.S. patent application Ser. No. 09/838,841) which is an important intermediate for preparing arbutin used as a whitening agent. Therefore, mono carbonylated benzene diols are useful for preparing an asymmetrically substituted benzene diol derivative which is industrially useful.

As an example of mono carbonylation of benzene diol, various processes are known as follows for a process for mono acetylation of hydroquinone.

1. Eur. Pat. Ep 178,929B, Celenase company
2. Eur. Pat. Ep 167,464B, Rhone-Pounenc company
3. Chem. Ind. (London), 1982, (24), 1000 Stering-Winthrop company The process (1) of Celenase company is characterized in that 4-acetyl phenol is synthesized by the Fries rearrangement of phenyl acetate prepared from the acetylation of phenol and it is oxidized with hydrogen peroxide by "Baeyer-Villiger" reaction to synthesize 4-acetyl hydroquinone. In the above process, hydrogen fluoride which is hard to handle in the Fries rearrangement reaction is used, and the yield of oxidation is below 60%.

The process (2) of Rhone-Poulenc company is characterized in that mono acetyl hydroquinone is synthesized by the ester interchange between hydroquinone and an excessive amount of diacetyl hydroquinone. However, It is not easy for separating excess diacetyl hydroquinone in the industrial process.

The process (3) of Stering-Winthrop company is characterized in that hydroquinone is reacted with acid anhydride in the presence of an organic base. Since hydroquinone has two equivalent hydroxyl groups, in case of monoacylation of hydroquinone, if one use a general method of acylation, monoacylated compounds are produced, the yield is low due to the excess production of diacylated hydroquinone and by the reaction with the acids resulted from using the organic bases, a salt can be produced. To remove the salt, it should be washed using water, so that a large amount of waste water is produced.

As described above, the above described processes are not proper for preparing mono carbonylated benzene diol in both economical and industrial basis.

SUMMARY OF THE INVENTION

Accordingly, it is an object of the present invention to provide a new and economical process for a monoprotection of benzene diol in high yield based on a simple preparation process without any organic or inorganic bases.

It is another object of the present invention to provide a process for a mono carbonylation of a benzenediol of the formula (I) which is characterized in that a benzene diol of the formula (II) is reacted with an acid anhyride or carbonyl halide of the formula (III) without any organic or inorganic bases for thereby producing a monocarbonylated benzene-diol of the formula (I):

wherein R is hydrogen, $C_1$–$C_{15}$ alkyl group, cyclic alkyl group, aryl group, alkoxy group, aryloxy group, dialkylamino group, alkylarylamino group or diarylamino group, and X is a general leaving group such as fluoride, chloride, bromide, iodide and acetoxy, etc.

An acyl group substituted by adding acid anhydride or carbonylhalide to an excessive amount of benzene diol/acetic acid solution decreases an electron density of benzene ring for thereby synthesizing mono carbonyl hydroquinone by limiting the production of dicarbonyl hydroquinone. Since benzene diol which is used in excess is a strong polar substance, by using a non-polar solvent, it is easy to retrieve benzene diol and refine mono carbonyl benzene diol.

The amount of benzene diol is 1.1–10 equivalent weight compared to acid anhydride, but preferably it is 2–5 equivalent weight.

The reaction temperature is from room temperature to 300° C., and from 50° C. to 150° C. is desirable.

A solvent capable of dissolving hydroquinone at reaction temperature is selected from the group consisting of tetrahydrofuran, 1,4-dioxane, acetonitrile ethyleneglycol dimethylether, ethyleneglycol dibutylether, diethyleneglycol dimethylether and triethyleneglycol dimethyether and diisopropylether.

DETAILED DESCRIPTION OF THE PREFERRED EXAMPLES

The present invention will be implemented by the following detailed examples. The following examples are provided for only illustrative purposes, and the descriptions of the present invention do not limit the examples.

EXAMPLES

Example 1

Preparation of Monoacetyl Hydroquinone

In the solution of 220 g(2 mol) of hydroquinone in 500 ml of acetic acid, 102 g(1 mol) of acetic anhydride was drop-added for one hour while agitating the solution at 110° C. The mixture was maintained at 110° C. for two hours, and acetic acid was distilled under vacuum. 1 liter of toluene was added to the reaction mixture and the unreacted excess hydroquinone was filtered and collected (recovered amount: 110 g, recycled without any purification process). A desired monoacetyl hydroquinone was obtained by evaporating the residue under vacuum. (Yield: 149.1 g(98%). mp: 60–62° C., $^1$H-NMR(200 MHz, $CDCl_3$, ppm) 2.25(s, 3H), 5.78 (br, 1H), 6.70 (d,2H), 6.88 (d, 2H).

Example 2
Preparation of Mono Acetyl Resorcinol

In the solution of 220 g(2 mol) of resorcinol in 500 ml of acetic acid, 102 g(1 mol) of acetic anhydride was drop-added for one hour while agitating the solution at 110° C. The mixture was maintained at 110° C. for two hours, and acetic acid was distilled under vacuum. 1 liter of toluene was added to the reaction mixture and the unreacted excess hydroquinone was filtered and collected (recovered amount: 110 g, recycled without any purification process). A desired mono acetyl resorcinol was obtained by evaporating the residue under vacuum. (Yield: 149.7 g(98%). mp: oil, $^1$H-NMR(200 MHz, CDCl$_3$, ppm) 2.29(s, 3H), 6.53–6.67 (m, 4H), 7.18 (t. 1H)

Example 3
Preparation of Mono Acetyl Catechol

In the solution of 220 g(2 mol) of catechol in 500 ml of acetic acid, 102 g(1 mol) of acetic anhydride was drop-added for one hour while agitating the solution at 110° C. The mixture was maintained at 110° C. for two hours, and diethylene glycol dibutyl ether was distilled under vacuum. 1 Liter of toluene was added to the reaction mixture and cooled to 0° C. and then the unreacted excess hydroquinone was filtered and collected (recovered amount: 110 g, recycled without any purification process). A desired mono acetyl catechol was obtained by evaporating the residue in vacuum. (Yield: 149.0 g(98%). mp: oil. $^1$H-NMR(200 MHz, CDCl$_3$, ppm) 2.33(s, 3H), 5.81 (br, 1H), 6.83–7.18 (m, 4H).

Example 4
Preparation of Mono Benzoyl Hydroquinone

In the solution of 220 g(2 mol) of hydroquinone in 500 ml of glycol dibutyl ether, 140.5 g(1 mol) of benzoyl chloride was drop-added for one hour while agitating the solution at 110° C. The mixture was maintained at 110° C. for two hours, and diethylene glycol dibutyl ether was distilled under vacuum. 1 liter of methylene chloride was added to the reaction mixture, and the unreacted excess hydroquinone was filtered and collected (recovered amount: 110 g, recycled without any purification process). A desired mono benzoyl hydroquinone was obtained by evaporating the residue under vacuum. (Yield: 207.0 g(97%). mp: 160–162° C., $^1$H-NMR(300 MHz, CDCl$_3$, ppm) 5.80 (br, 1H), 6.72 (d,2H), 6.89 (d, 2H), 7.44–7.48 (m, 1H), 7.49–7.56 (m, 1H), 8.16 (d, 2H).

Example 5
Preparation of Mono Ethoxycarbonyl Hydroquinone

In the solution of 220 g(2 mol) of hydroquinone in 500 ml of acetic acid, 108.5 g(1 mol) of ethyl chloroformate was drop-added for one hour while agitating the solution at 110° C. The mixture was maintained at 110° C. for two hours, and acetic acid was distilled under vacuum. 1 liter of methylene chloride was added to the reaction mixture, and the unreacted excess hydroquinone was filtered and collected (recoverd amount: 110 g, recycled without any purification process). A desired mono ethoxycarbonyl hydroquinone was obtained by evaporating the residue under vacuum. (Yield: 164.6 g(98%). mp: 81–82° C., $^1$H-NMR(200 MHz, CDCl$_3$, ppm) 1.38 (t, 3H), 4.31 (q, 2H), 5.57 (br, 1H) 6.72 (d, 2H), 6.98 (d, 2H).

Example 6
Preparation of Mono N,N-dimethylcarbamyl Hydroquinone

In the solution of 220 g(2 mol) of hydroquinone in 500 ml of acetic acid, 107.5 g(1 mol) of dimethylcarbamyl chloride was drop-added for one hour while agitating the solution at 110° C. The mixture was maintained at 110° C. for two hours, and acetic acid was distilled under vacuum. 1 liter of methylene chloride was added to the reaction mixture, and the unreacted excess hydroquinone was filtered and collected (recoverd amount: 110 g, recycled without any purification process). A desired mono N,N-dimethylcarbamyl hydroquinone was obtained by evaporating the residue under vacuum. (Yield: 178.6 g(98%). mp: 144–146° C., $^1$H-NMR(200 MHz, CDCl$_3$, ppm) 3.05 (d, 6H), 6.59 (d, 2H), 6.80 (br, 1H) 6.82 (d, 2H).

As described above, in the present invention, it is possible to minimize the production of dicarbonyl hydroquinone(1) without using any organic or inorganic bases (2) and obtain mono protected hydroquinone in high yield (3) without production of waste water (4).

What is claimed is:

1. A process for a mono carbonylation of a benzenediol of the formula (I) characterized in that a benzene diol of the formula (II) is reacted with an acid anhydride or carbonyl halide of the formula (III) without any organic or inorganic bases for thereby producing a monocarbonylated benzene diol of the formula (I):

wherein R is hydrogen, C$_1$–C$_{15}$ alkyl group, cyclic alkyl group, aryl group, alkoxy group, aryloxy group, dialkylamino group, alkylarylamino group or diarylamino group, and X is a general leaving group such as fluoride, chloride, bromide, iodide and acetoxy.

2. The process of claim 1, wherein an excessive amount of the benzenediol of the formula (II) is used with respect to an acyl compound of the formula (III).

3. The process of claim 1, wherein 1.1–20 equivalent weight of the benzene diol of the formula (II) is used with respect to one equivalent weight of the acyl compound of the formula (III).

4. The process of claim 2, wherein 1.1–20 equivalent weigh of the benzene diol of the formula (II) is used with respect to one equivalent weigh of the acyl compound of the formula (III).

5. The process of one selected from claim 1, wherein 2–5 equivalent weight of the benzene diol of the formula (II) which is used in excess with respect to one equivalent weight of the acyl compound of the formula (III).

6. The process of one selected from claim 2, wherein 2–5 equivalent weight of the benzene diol of the formula (II) which is used in excess with respect to one equivalent weight of the acyl compound of the formula (III).

7. The process of one selected from claim 3, wherein 2–5 equivalent weight of the benzene diol of the formula (III) which is used in excess with respect to one equivalent weight of the acyl compound of the formula (III).

8. The process of one selected from claim 1, wherein the unreacted benzene diol of the formula (II) is recovered using a non-polar solvent.

9. The process of one selected from claim 2, wherein the unreacted benzene diol of the formula (II) is recovered using a non-polar solvent.

10. The process of one selected from claim 3, wherein the unreacted benzene diol of the formula (II) is recovered using a non-polar solvent.

11. The process of claim 8, wherein said non-polar solvent is more than one solvent selected from the group consisting of benzene, toluene, xylene, ether, hexane, petroleum ether, methylene chloride and chloroform.

12. The process of claim 1, wherein as a reaction solvent, more than one solvent selected from the group consisting of tetrahydrofuran, 1,4-dioxane, acetonitrile, ethyleneglycol dimethylether, ethyleneglycol dibutylether, diethyleneglycol dimethylether, triethyleneglycol dimethylether and diisopropylether is used.

* * * * *